United States Patent [19]
Christoudias

[11] Patent Number: 5,817,112
[45] Date of Patent: Oct. 6, 1998

[54] CHRISTOUDIAS FASCIAL CLOSURE DEVICE

[75] Inventor: George C. Christoudias, Saddle River, N.J.

[73] Assignee: Surgical Inventions & Innovations, Inc

[21] Appl. No.: 934,619

[22] Filed: Sep. 22, 1997

[51] Int. Cl.[6] .................................................. A61B 17/04
[52] U.S. Cl. .......................................... 606/148; 606/139
[58] Field of Search ................................... 606/139, 144, 606/145, 147, 148

[56] References Cited

U.S. PATENT DOCUMENTS

| | | | |
|---|---|---|---|
| 5,320,629 | 6/1994 | Noda et al. | 606/148 |
| 5,387,227 | 2/1995 | Grice | 606/148 |
| 5,391,174 | 2/1995 | Weston | 606/148 |
| 5,433,722 | 7/1995 | Sharpe et al. | 606/148 |
| 5,462,560 | 10/1995 | Stevens | 606/148 |
| 5,499,991 | 3/1996 | Garman et al. | 606/148 |
| 5,562,683 | 10/1996 | Chan | 606/148 |
| 5,562,688 | 10/1996 | Riza | 606/148 |

Primary Examiner—Gary Jackson
Attorney, Agent, or Firm—Richard A. Joel

[57] ABSTRACT

The Christoudias fascial closure device comprises an elongated penetrating instrument having a sharp conical trapping end, an elongated hollow body extending rearwardly from the solid trapping end, a stylet movable within the hollow body and an upper manipulating end including a handle mounted on the stylet and a flange grip extending outwardly from the hollow body. An opening is located in the wall of the hollow body near the conical end and a straight spring wire protrudes outwardly therefrom when the handle is compressed. The spring wire is affixed at one end to the conical tip and at the other end to the forward portion of the stylet within the hollow body. The spring wire grasps a thread within the peritoneal cavity in order to pass the thread through the tissues to the outside. The device is then introduced into the cavity in the same manner through the same layers of tissues at the opposite end of the wound in order to close the wound by grasping the other end of the thread. The present device thus discloses a method and instrument for fascial closure of wounds in a simple, efficient, safe and expeditious manner.

8 Claims, 5 Drawing Sheets

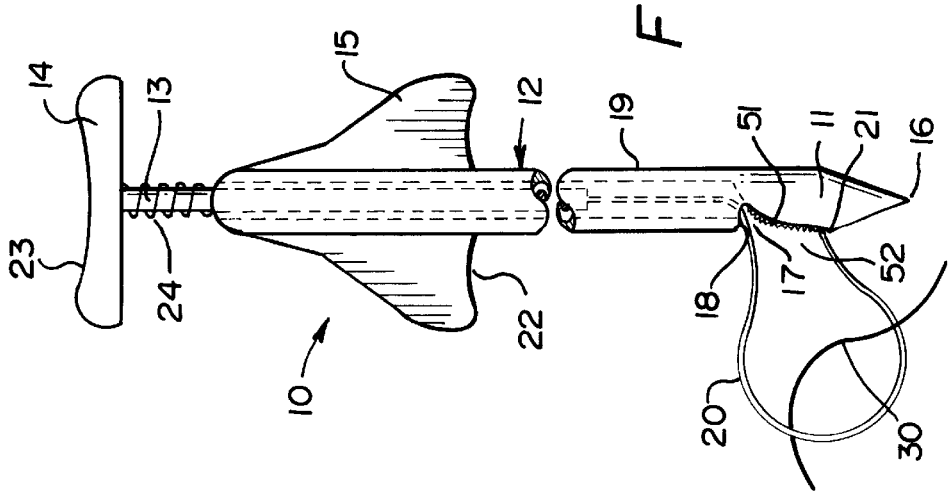

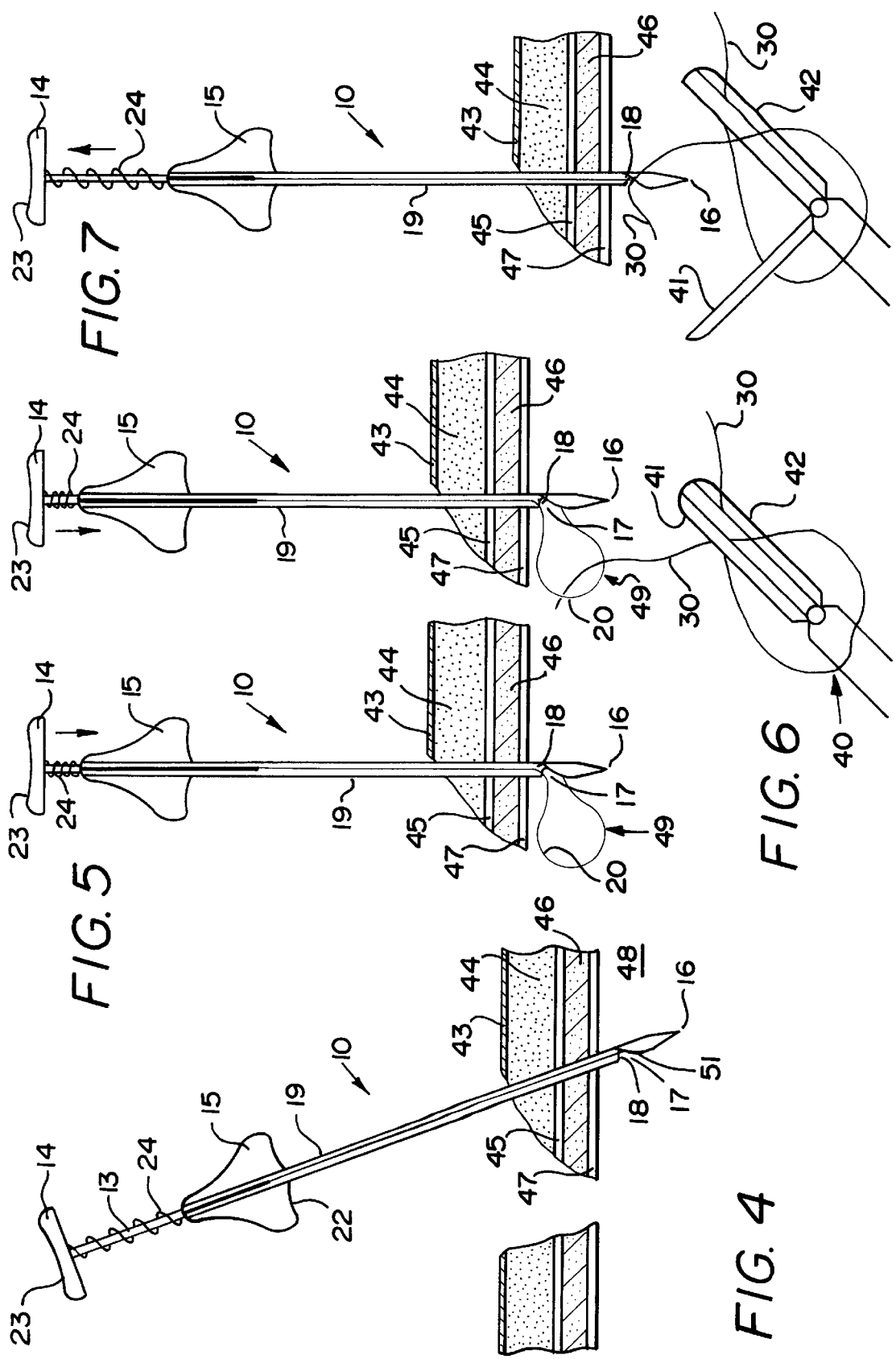

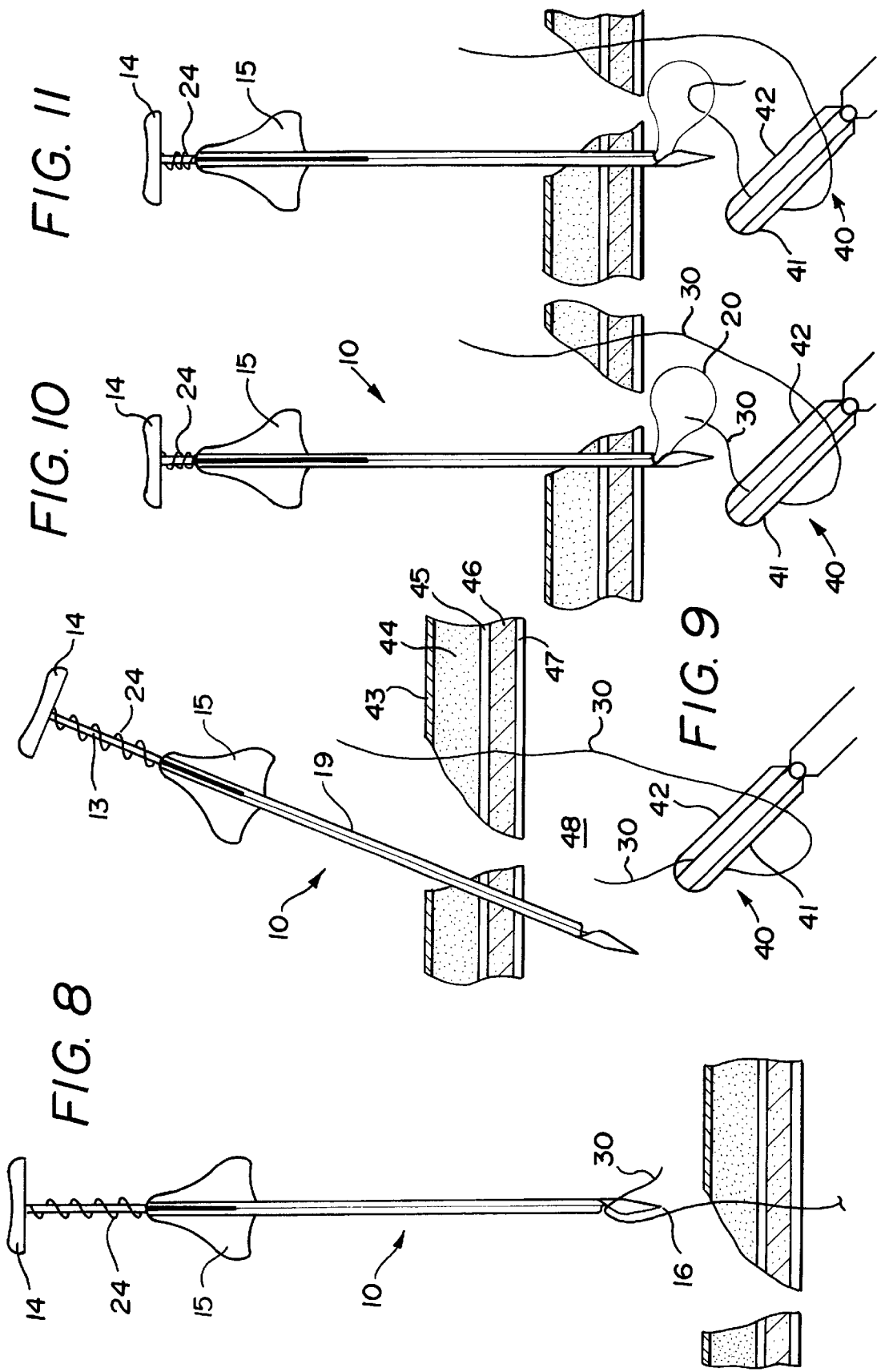

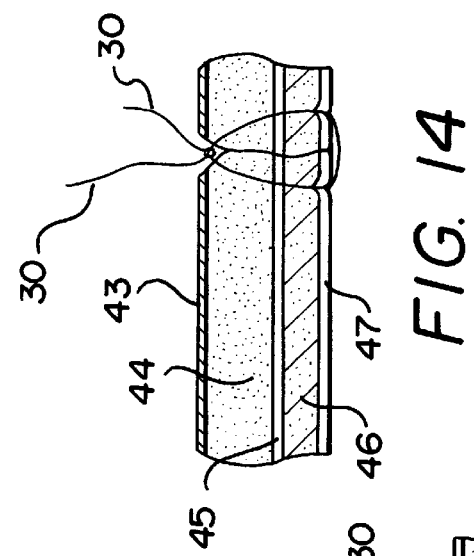
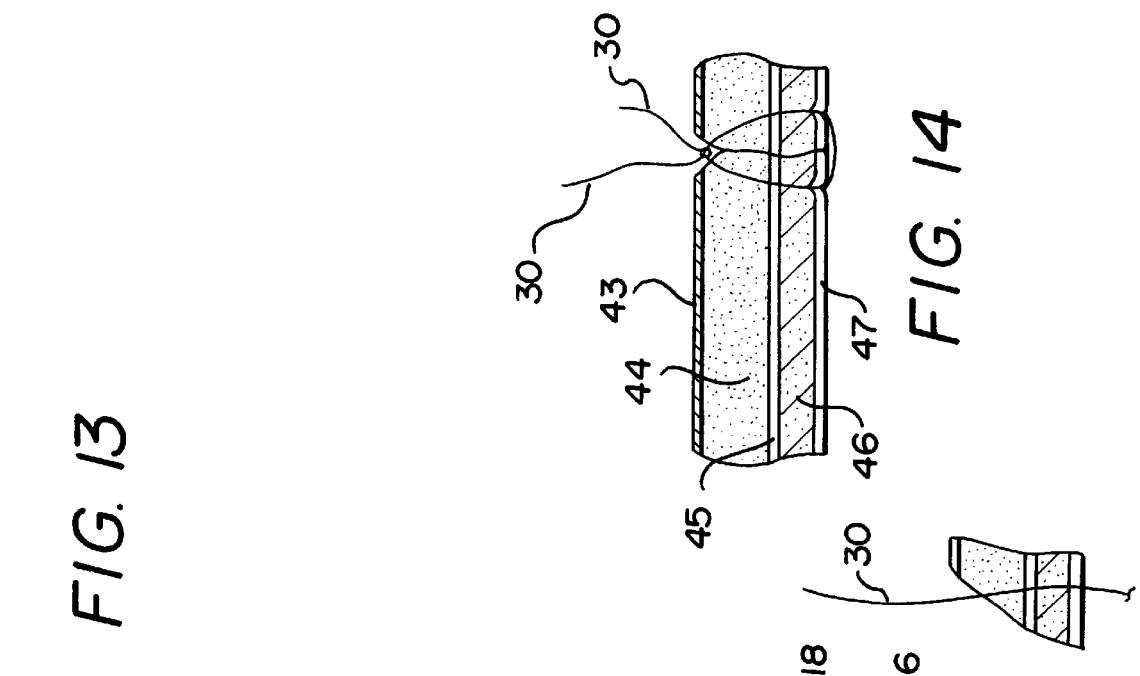
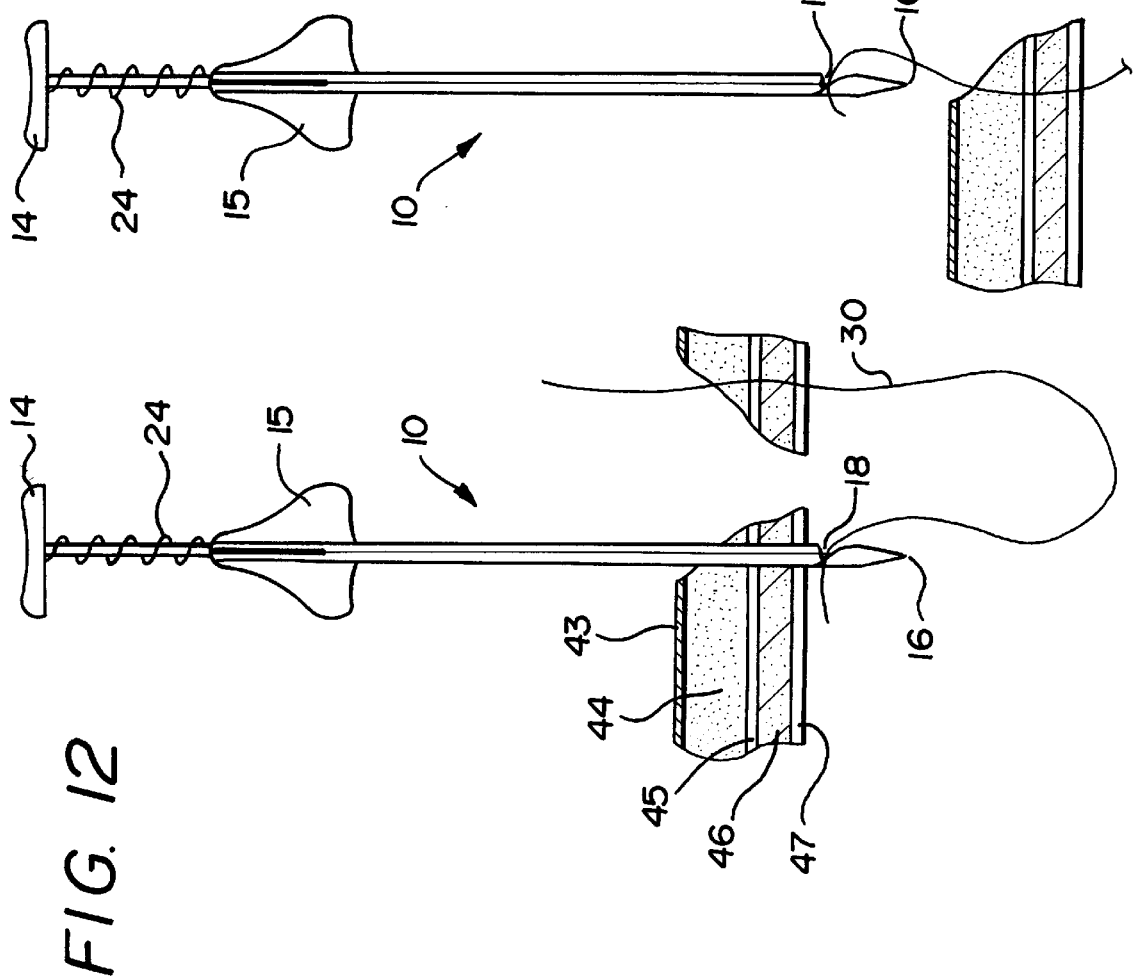

CHRISTOUDIAS FASCIAL CLOSURE DEVICE

BACKGROUND OF THE INVENTION

With the ever increasing number of intra-abdominal surgical procedures being performed laparoscopically, a number of problems have surfaced. For example, herniation of the entry wounds is a late complication that has to be prevented. In order to prevent the herniation of stab wounds, particularly 10mm in length or larger, such wounds should be closed at the fascial layer. Numerous instruments have been developed which are too complicated to use, time consuming, dangerous and just too expensive. The present invention discloses a method and instrument for fascial closure of wounds in a simple, efficient, safe and expeditious manner.

Among the prior art devices is the "Endoclose" marketed by U.S. Surgical Corporation. The device or instrument comprises a spring loaded crochet needle within a hollow needle having a sharp point. The crochet needle is fully retracted by the action of a spring wire. The groove of the crochet needle in conjunction with the periphery of the hollow needle form a trap in which a thread is engaged. The "Endoclose" with the thread trapped in place is then forced through the fascia to be sutured closed into the abdomen. The end of the suture is then grasped with a laparoscopic instrument within the abdominal cavity and the crochet needle extended (moved beyond the sharp point of the hollow needle) opening up the trap and releasing the thread. The crochet needle is then allowed to return to the neutral position and the "Endoclose" instrument removed from the abdomen and then reinserted through the opposing segment of the fascia to be sutured closed. The crochet needle is fully extended opening the trap, the thread held by the laparoscopic instrument is guided into the groove of the crochet needle and the crochet needle retracted to the neutral position engaging the thread in the trap. The "Endoclose" is then removed from the abdominal cavity pulling with it the end of the thread which will form a loop with the opposing end of the thread when tied, closing the opposing edges of the fascia.

There are distinct disadvantages with the "Endoclose" which are not present in the double pull fascial closure device of the present invention.

The undesirable features of the "Endoclose" are 1) loading the thread in decreased lighting is extremely frustrating; 2) the dull edge of the crochet needle component makes penetration of the fascia difficult. This necessitates the application of a considerable amount of force on the "Endoclose" during penetration with risk of injury to the underlying intra-abdominal organs when the tissues "give" suddenly, if extreme caution is not exercised by the operator; 3) engaging the thread intra-abdominally by the crochet needle is very difficult because of the small size of the groove in which the thread has to be placed. This becomes, at times, frustrating especially for the non expert laparoscopist; and, 4) entrapment of tissue particles into the groove may functionally fill and eliminate the groove of the crochet needle making the difficult task of trapping the thread close to impossible.

Another prior art device for fascial closure marketed by the Apple Medical Corporation is comprised of three elements: 1) a hollow needle with a smooth edged penetrating end; 2) a complimentary solid stylet which is inserted into the hollow needle and locks onto it forming a functional penetrating needle with a sharp point; 2) a thread retrieving element made of a spring loop wire attached to the penetrating end. This latter element fits into the hollow needle. After insertion into the needle, the spring loop wire is retracted into the lumen of the needle until it is pushed through the smooth edged end of the hollow needle. When exiting the hollow needle, the spring loop wire opens up and a thread can be advanced through the loop. Withdrawal of the thread retrieving part will again close the loop and trap the thread.

The Apple device or instrument is comprised of a stylet which is inserted into the hollow needle forming a functional sharp point penetrating needle. The needle is inserted through one side of the fascia to be sutured closed into the abdomen and the stylet removed. A thread is then threaded into the hollow needle and advanced through it into the abdominal cavity. The end of the thread is engaged by a laparoscopic instrument as the needle is withdrawn from the abdominal cavity. The stylet is reinserted into the hollow needle once again forming a functional sharp point penetrating needle. The needle is inserted through the opposing side of the fascia to be sutured closed into the abdomen and then stylet is then removed. The thread retrieving element is inserted into the abdomen through the hollow needle and the thread is placed into the loop of the spring wire and engaged by withdrawing the thread retrieving element. The needle and retrieving element are withdrawn delivering the end of the thread to the outside. The delivered end of the thread is tied with the other end of the thread to close the opposing edges of the fascia.

The Apple instrument is virtually impossible to use because of the following undesirable features: 1) There are much too many steps involved in performing the simple task of passing a thread through two opposing edges of tissues; 2) finding a surgeon patient enough to put up with the frustration of pushing a thin thread through a 5½" needle is near impossible. Applicant has personally tried this only once and gave it up immediately when the thread became stuck in the needle and would not advance.; and 3) it is too time consuming.

A plethora of other devices for stab wound fascial closures have been developed over the recent past which involve the insertion of the thread through the one side of the fascia to be sutured closed and then retrieved, passed through the opposing side of the fascia. None of these devices has the advantages of the present invention.

SUMMARY OF THE INVENTION

This invention relates to fascial closure devices and particularly to a new and improved method and device for the fascial closure of wounds.

The Christoudias fascial closure device comprises an elongated penetrating instrument having a sharp conical tip, a hollow body and a stylet moveable within the hollow body. An aperture is located in the hollow wall adjacent the solid tip wherein a spring wire protrudes outwardly therefrom. The spring wire is mounted internally at one end to the solid tip and at the other end to the forward end of the stylet. The upper end of the stylet extends outwardly from the hollow body and includes a handle mounted thereto to manipulate the spring wire which protrudes outwardly therefrom in a loop. A grasping flange on the hollow body aids in manipulating the device.

The fascial closure device is inserted through the tissue layers into the peritoneal cavity in order to seize a thread which is brought into proximity by a grasper. The stylet is then moved rearwardly trapping the thread within the device. The thread is drawn through the tissues by withdrawing the closure device. The fascial closure device is then introduced into the cavity on the opposite side of the wound and the process is repeated in order to close the wound. Thus, the invention disclosed herein provides a method and instrument for the fascial closure of wounds in a simple, efficient, safe and expeditious manner.

Accordingly, an object of this invention is to provide a new and improved method and device for the fascial closure of wounds.

Another object of this invention is to provide a new and improved instrument comprising a hollow needle and cooperating stylet which permit the grasping of threads within a body cavity to close wounds.

A more specific object of this invention is to provide a new and improved fascial closure instrument which permits the rapid and efficient trapping of threads within a body cavity to close wounds in a simple and safe manner.

BRIEF DESCRIPTION OF THE DRAWINGS

The above and objects and advantages of the invention may be more clearly seen when viewed in conjunction with the accompanying drawings wherein:

FIG. 1 is a front view of the invention with the spring wire extended;

FIG. 2 is a front view of the invention with the handle fully extended and the spring wire grasping a thread;

FIG. 3 is a longitudinal section take along the line 3—3 of FIG. 2 while FIG. 3a is a section taken along the line 3a—3a FIG. 2;

FIG. 4. discloses the device in use wherein the device is inserted through the tissues and through the peritoneal cavity;

FIG. 5 discloses the device in compressed state with the spring loop extended outwardly from the side opening;

FIG. 6 discloses a thread held by the Maritsa Tissue Approximator Double Grasper being inserted within the spring wire loop;

FIG. 7 discloses the grasper draw open and the thread being held by the fascial closer device;

FIG. 8 discloses the thread being pulled outwardly through the tissues to the outside;

FIG. 9 discloses the device being entered through the opposite end of the wound;

FIG. 10 discloses the device in a compressed state with the wire loop extending outwardly towards the thread being held by the Maritsa Tissue Approximator Double Grasper;

FIG. 11 discloses the spring loop inserted the thread held by the grasper;

FIG. 12 discloses the fascial closure device in a extended position grasping the thread;

FIG. 13 discloses the device being removed from the tissue pulling the thread through the tissue;

FIG. 14 discloses the thread being tied to close the wound; and,

DETAILED DESCRIPTION OF THE INVENTION

Figure 16:
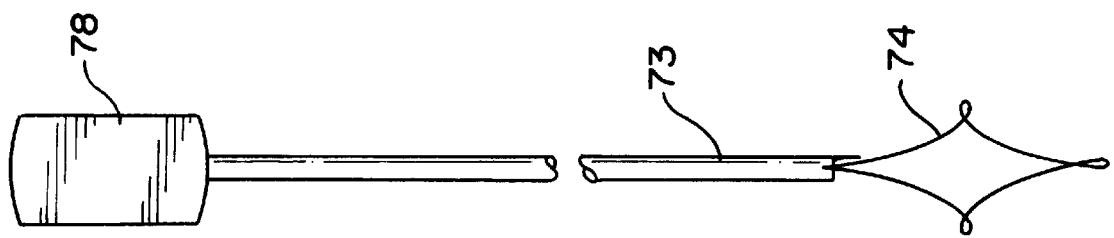

The Christoudias fascial closure device 10 comprises an elongated penetrating instrument with a sharp conical trapping end 11 having an elongated hollow body 12, a stylet 13, and a manipulating end including a handle 14 and a flanged grip 15.

The trapping end 11 is comprised of a sharp solid needle tip 16 leading to a tubular hollow needle 12. At the junction of the solid and tubular portions 16 and 12, there is an opening 17 in the needle wall 19 communicating with the lumen 18 (tubular compartment) of the needle 12. This opening 17 allows the retraction and propulsion of a spring wire 20 therethrough. The solid point of the trapping end 11 has a conical shape ending in a sharp tip 16. The conical point 16 extends in a curvilinear fashion to meet the tubular needle 12 forming a convex shaped surface facing the opening of the tubular needle 12. The lower end of a straight spring wire 20 is attached at the base 21 of the conical point and at the side of the needle opening 17. This wire 20 passes over the convex surface 35 of the solid tip 11 and into the lumen 18 of the tubular needle 12 where it advances and ends on a shaft or stylet 13 to which it is securely fixed. The stylet 13 is movable within the lumen 18 and along the axis of the needle 12. Motion of the stylet 13 is effected by manipulation of the handle 14 between fully extended and fully retracted positions.

The shaft 12 comprises of a length of tubular needle which accommodates the wire 20 and stylet 13 of the device 10. The gripping member 15 comprises a winged attachment on the upper end of the tubular needle 12 with diametrically opposite finger depressions 22 for the index and middle fingers. The handle 14 includes a transverse bar at the end of the stylet 13 which connects at right angles and includes a central depression 23 to accommodate the thumb. Additionally, the assembly includes a coiled spring wire 24 which rests over the stylet 13 and between the handle 14 and the winged attachment 15. This spring wire 24, when, at rest position, keeps the instrument 10 in a fully extended position by spreading the platform handle 14 of the stylet 13 apart from the winged attachment. By compressing the handle 14 between the thumb (depression) platform 23 and the finger depression winged attachment 15 in a fully retracted position, the stylet 13 is advanced towards the sharp end of the instrument forcing the straight spring wire 20 through the opening of the needle in a looped state as shown in FIG. 1. At the same time, this compression forces the coiled spring wire 24 into a loaded contracted state.

A thread 30 is passed through the loop of the spring wire 20 and the compression pressure on the handle 14 is released allowing the loaded coiled spring wire 24 to force the handle 14 into a fully extended position as shown in FIG. 2, with the stylet 13 moving away from the sharp end 11 of the instrument 10 and pulling with it the straight wire 20 into its original position. The straight wire 20 traps the thread 30 between it and the convex surface of the trapping end 11 of the instrument 10. Compression of the handle 14 in a fully retracted position advances the straight spring wire 20 into a looped position and frees the thread 30.

In actual practice, the fascial closure device 10 is used for the closure of the fascia through a stab wound in the following manner:

The thread 30 to be used for the closure is loaded onto the Maritsa Tissue Approximator double grasper 40 (U.S. Pat. No. 5,403,332) by engaging the two ends of the thread 30 in the two independently operated jaws 41, 42. The loaded double grasper 40 is then inserted into the body cavity through a separate port. This process is adequately described in the patent and hence is not described at length herein.

The fascial closure device 10 is then entered through the subcutaneous tissue 44, muscle layers 45, fascia 46 and peritoneum 47 into the peritoneal cavity, (FIG. 4). The device 10 is advanced until the entire trapping end 11 is inside the peritoneal cavity 48. The handle 14 of the device 10 is then compressed forcing the spring wire 20 in the abdomen into a looped state, see FIG. 5. The grasper 40 with the thread 30 is then advanced close to the wire loop 49 and one of the thread ends 30 is inserted into the loop 49, see FIG. 6.

The compression on the handle 14 and member 15 then released. This causes the spring wire 20 to be pulled back to its original position, trapping the thread 30 which is released from the double grasper 40 by opening the corresponding jaw 41 of said grasper 40 see FIG. 7.

The fascial closure device 10 is then pulled out of the peritoneal cavity 48 passing the thread 30 through the tissues to the outside. The thread 30 is then disengaged from the device 10. The device 10 is subsequently introduced in the same manner through the same layers of tissues at the opposite side of the stab wound as in FIG. 9.

In a similar fashion with the opposite side, the spring wire 20 is looped, FIG. 10, the thread end advanced through the loop 49, the loop 49 closed, trapping the second end of the thread 30 which is then released from the grasper 40, FIG. 12. The device 10 is then pulled out of the abdominal cavity 48, drawing the second end of the thread 30 through the tissues FIG. 13. The thread 30 is then tied as shown in FIG. 14, approximating the tissues which is the objective of this device.

Figure 15:
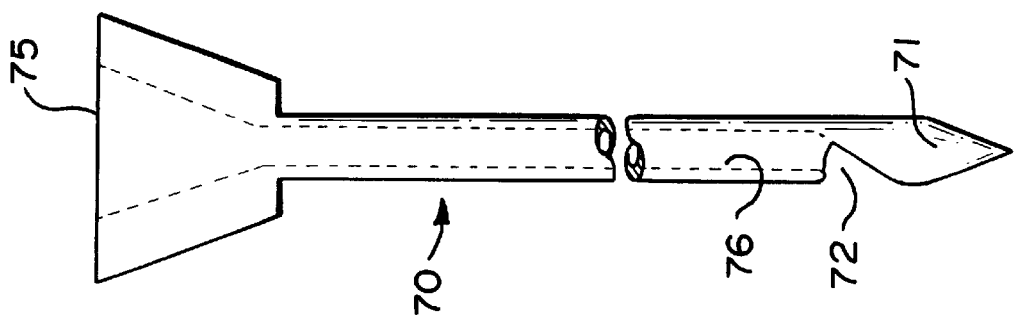
FIG. 15 discloses an alternate embodiment of the device which includes the stylet shown in FIG. 16.

An alternate embodiment shown in FIGS. 15 and 16 comprises a hollow needle 70 with a sharp solid tip 71 and a side port 72 or opening just proximal to said tip 71 and a stylet 73 with a spring loop wire 74 attached to one end. The stylet 73 is inserted into the hollow needle 70 through the open end 75 and advanced until the wire loop 74 exits from the lumen 76 through the side port 72 projecting in an open state near the sharp solid tip 71. A thread end can then be inserted into the loop by a grasper (not shown) and the stylet 73 moved with hand 78 to withdraw the loop wire 74 back into the lumen 76 of the needle 70 trapping the thread. This alternate embodiment is used in the same manner and sequence as the preferred embodiment previously described. While the invention has been explained by a detailed description of certain specific embodiments, it is understood that various modifications and substitutions can be made in any of them within the scope of the appended claims which are intended also to include equivalents of such embodiments.

What is claimed, is:

1. The Christoudias fascial closure device for closing wounds by grasping and maneuvering threads within a body cavity comprising:

an elongated penetrating needle having a hollow body, a sharp conical trapping end and a side opening in the hollow body adjacent the conical trapping end;

a stylet having a solid elongated body, including a forward end and a rear end slidable within the hollow body;

a spring wire attached at one end to the forward end of the stylet within the hollow body and at the other end to the conical trapping end, said wire protruding from the side opening; and, a handle mounted to the rear end of the stylet for retracting the stylet causing the protruding spring wire to grasp a thread within the body cavity said thread being drawn through the fascial layer by movement of the needle to close the wound.

2. The Christoudias fascial closure device for closing wounds by grasping and maneuvering threads with a body cavity comprising in accordance with claim 1 further including:

a coiled spring mounted about the stylet and engaging the handle to normally urge the handle outwardly causing the spring wire to retract within the side opening.

3. The Christoudias fascial closure device for closing wounds by grasping and maneuvering threads with a body cavity in accordance with claim 1 further including:

flanges extending outwardly on opposite sides of the hollow body and engaging the coiled spring at one end to facilitate manipulation of the hollow body in conjunction with the stylet.

4. The Christoudias fascial closure device for closing wounds by grasping and maneuvering threads with a body cavity in accordance with claim 1 wherein:

the conical trapping end comprises a solid body forming a sharp tip; and, the side opening comprises an inwardly curved lower portion having a plurality of detents along the surface thereof to assist in grasping and engaging firmly the thread between said spring wire and the detent surface as the stylet is withdrawn upwardly within the hollow body.

5. The Christoudias fascial closure device for closing wounds by grasping and maneuvering threads with a body cavity comprising:

a hollow needle having a sharp solid tip at one end, an elongated hollow body having a side port opening adjacent the solid tip and an outwardly flared end portion having an enlarged opening; and, a stylet having an enlarged handle at one end to fit within the flared end portion, an elongated stem extending from the handle at one end and slidable within the hollow body by withdrawing the stylet within the hollow body and a loop wire mounted to the other end of the stem and extending outwardly from the side port to snare a thread within the loop as the handle is moved upwardly.

6. The Christoudias fascial closure device for closing wounds by grasping and maneuvering threads with a body cavity in accordance with claim 3:

the needle includes flanges slidably mounted to the hollow body and extending downwardly and outwardly for a predetermined distance and then curving inwardly to the hollow body forming a manipulating portion with the handle having a curved surface so that the device can be manipulated with one hand.

7. The method of using the Christoudias fascial closure device comprising the steps of:

providing a Christoudias fascial closure device for closing wounds by suturing the tissues, said device including a solid tip, a hollow body and an outwardly extending flange and a stylet having a spring urged handle at one end and being slidable within the hollow body and having a spring wire mounted to the stylet at one end and the solid tip at one end and extending outwardly in a loop from a side port in the hollow body;

inserting the device tip first through the tissues to be sutured into the body cavity;

providing a thread within the body cavity;

directing one end of the thread within the wire loop;

releasing the handle to grasp the thread within the side port;

withdrawing the device with the grasped thread through the penetrated tissues and thus advancing the thread through said tissues;

releasing the thread from the device;

repeating the steps through the opposing side of the wound engaging and advancing the other end of the thread through the opposing side of the wound; and, tying the two ends of the thread and thus closing the wound by approximating and securing together the two opposing sides of the wound.

8. The method in accordance with claim 7 wherein:

the hollow body includes an enlarged aperture at the end opposite the solid tip and the stylet includes an enlarged handle which is removably positioned within the aperture and said handle is manually manipulated to draw the thread within the side port.

* * * * *